US011450977B2

(12) United States Patent
Shah (10) Patent No.: US 11,450,977 B2
(45) Date of Patent: Sep. 20, 2022

(54) IMPLANTABLE CONNECTOR INCLUDING AT LEAST ONE ELECTRICAL COMPONENT

(71) Applicant: Verily Life Sciences LLC, South San Francisco, CA (US)

(72) Inventor: Kedar Shah, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 78 days.

(21) Appl. No.: 16/824,013

(22) Filed: Mar. 19, 2020

(65) Prior Publication Data

US 2020/0220285 A1 Jul. 9, 2020

Related U.S. Application Data

(63) Continuation of application No. 15/923,490, filed on Mar. 16, 2018, now Pat. No. 10,608,354.
(Continued)

(51) Int. Cl.
*H01R 12/52* (2011.01)
*H01R 13/52* (2006.01)
(Continued)

(52) U.S. Cl.
CPC .......... *H01R 12/52* (2013.01); *A61B 5/0031* (2013.01); *A61B 5/14503* (2013.01); *A61B 5/686* (2013.01); *A61B 5/6846* (2013.01); *A61B 17/3468* (2013.01); *A61N 1/0551* (2013.01); *A61N 1/3752* (2013.01); *H01R 12/7082* (2013.01); *H01R 12/714* (2013.01);
(Continued)

(58) Field of Classification Search
None
See application file for complete search history.

(56) References Cited

U.S. PATENT DOCUMENTS 3,290,736 A    12/1966   Mann et al.
3,923,060 A * 12/1975   Ellinwood, Jr. ....... A61B 5/021
                                                                                                      604/891.1
(Continued)

FOREIGN PATENT DOCUMENTS

CN         103732284 A *   4/2014           A61B 5/0017
DE         102012010901     12/2012
(Continued)

OTHER PUBLICATIONS

U.S. Appl. No. 15/923,490 , "Ex Parte Quayle Action", May 31, 2019, 10 pages.
(Continued)

*Primary Examiner* — Timothy J. Dole
*Assistant Examiner* — Muhammed Azam
(74) *Attorney, Agent, or Firm* — Kilpatrick Townsend & Stockton LLP (57) ABSTRACT

An implantable connector for connecting an electronics package and a neural interface is made by way of a compressible contacts (e.g., a spring) that physical contacts a corresponding exposed bond pad. The compressible contact is held in compression with the exposed bond pad using a mechanical coupler. The compressible contact is physically separated and electrically isolated from other contacts by way of a compressible gasket. The compressible gasket is also held in compression using the mechanical coupler.

20 Claims, 4 Drawing Sheets

Related U.S. Application Data (60) Provisional application No. 62/475,365, filed on Mar. 23, 2017.

(51) Int. Cl.

| | | |
|---|---|---|
| *H01R 43/20* | (2006.01) | |
| *H05K 1/14* | (2006.01) | |
| *H05K 5/00* | (2006.01) | |
| *H05K 3/40* | (2006.01) | |
| *H05K 3/36* | (2006.01) | |
| *A61B 5/00* | (2006.01) | |
| *A61B 17/34* | (2006.01) | |
| *A61N 1/05* | (2006.01) | |
| *H01R 13/24* | (2006.01) | |
| *A61N 1/375* | (2006.01) | |
| *A61B 5/145* | (2006.01) | |
| *H01R 12/70* | (2011.01) | |
| *H01R 12/71* | (2011.01) | |
| *H05K 1/02* | (2006.01) | |
| *A61N 1/36* | (2006.01) | |
| *H05K 1/11* | (2006.01) | |
| *A61B 5/24* | (2021.01) | |

(52) U.S. Cl.
CPC ..... *H01R 13/2414* (2013.01); *H01R 13/2421* (2013.01); *H01R 13/521* (2013.01); *H01R 13/5219* (2013.01); *H01R 43/205* (2013.01); *H05K 1/02* (2013.01); *H05K 1/144* (2013.01); *H05K 3/368* (2013.01); *H05K 3/4007* (2013.01); *H05K 3/4015* (2013.01); *H05K 3/4038* (2013.01); *H05K 5/006* (2013.01); *H05K 5/0056* (2013.01); *H05K 5/0095* (2013.01); *A61B 5/14532* (2013.01); *A61B 5/24* (2021.01); *A61B 2560/063* (2013.01); *A61B 2562/0209* (2013.01); *A61B 2562/16* (2013.01); *A61B 2562/227* (2013.01); *A61N 1/3605* (2013.01); *A61N 1/3754* (2013.01); *H01R 2201/12* (2013.01); *H05K 1/112* (2013.01); *H05K 2201/0133* (2013.01); *H05K 2201/042* (2013.01); *H05K 2201/09163* (2013.01); *H05K 2201/09409* (2013.01); *H05K 2201/10265* (2013.01); *H05K 2201/10371* (2013.01); *H05K 2201/10393* (2013.01); *H05K 2201/10409* (2013.01); *H05K 2201/2018* (2013.01); *H05K 2201/2036* (2013.01)

(56) References Cited

U.S. PATENT DOCUMENTS

| | | | | |
|---|---|---|---|---|
| 4,003,379 | A * | 1/1977 | Ellinwood, Jr. | A61M 5/1723 604/891.1 |
| 4,076,955 | A * | 2/1978 | Gates, Jr. | H01L 23/49827 174/50.5 |
| 4,220,813 | A * | 9/1980 | Kyle | H01B 17/305 174/152 GM |
| 4,712,557 | A * | 12/1987 | Harris | A61N 1/3752 439/586 |
| 4,932,409 | A * | 6/1990 | Hirschberg | A61N 1/3752 607/36 |
| 4,934,366 | A * | 6/1990 | Truex | A61N 1/3752 607/37 |
| 5,109,320 | A * | 4/1992 | Bourdelaise | H05K 3/325 361/764 |
| 5,755,743 | A | 5/1998 | Volz et al. | |
| 5,817,984 | A * | 10/1998 | Taylor | A61N 1/3754 501/67 |
| 5,906,520 | A * | 5/1999 | Frinker | H01R 13/2421 439/841 |
| 5,993,269 | A * | 11/1999 | Ito | H01R 39/646 439/824 |
| 5,998,733 | A * | 12/1999 | Smith | H01L 23/045 257/E23.184 |
| 6,053,777 | A * | 4/2000 | Boyle | G01R 1/06 439/700 |
| 6,247,943 | B1 * | 6/2001 | Moga | H01R 13/2421 439/125 |
| 6,377,059 | B2 * | 4/2002 | Vinther | G01R 1/06722 324/72.5 |
| 6,963,780 | B2 | 11/2005 | Ruben et al. | |
| 7,214,068 | B2 | 5/2007 | Kronich et al. | |
| 7,520,753 | B1 * | 4/2009 | Mulligan | G01R 1/0466 439/591 |
| 8,096,838 | B2 | 1/2012 | Dilmaghanian | |
| 8,122,596 | B2 | 2/2012 | Maghribi et al. | |
| 8,162,684 | B1 * | 4/2012 | Sochor | H01R 13/025 439/289 |
| 8,267,708 | B1 * | 9/2012 | Sochor | H01R 13/2414 439/289 |
| 8,593,816 | B2 | 11/2013 | Iyer et al. | |
| 8,735,751 | B2 | 5/2014 | Rust | |
| 8,849,415 | B2 * | 9/2014 | Bedenbaugh | H01R 24/58 607/115 |
| 8,897,876 | B2 * | 11/2014 | Sundaramurthy | A61N 1/3752 607/37 |
| 8,995,141 | B1 * | 3/2015 | Rathi | H05K 3/32 361/752 |
| 9,403,023 | B2 * | 8/2016 | Markham | A61N 1/3754 |
| 9,431,742 | B2 | 8/2016 | DiFonzo et al. | |
| 9,782,942 | B2 * | 10/2017 | Linhardt | B29D 11/00038 |
| 10,098,574 | B1 | 10/2018 | Kam | |
| 10,608,354 | B2 * | 3/2020 | Shah | H01R 12/7082 |
| 10,693,257 | B2 * | 6/2020 | Kimmig | A61N 1/3752 |
| 2003/0050549 | A1 * | 3/2003 | Sochor | H01R 24/58 600/378 |
| 2003/0124895 | A1 * | 7/2003 | Winter | H01R 13/2421 439/219 |
| 2003/0176113 | A1 * | 9/2003 | Sasaki | H01R 13/2421 439/700 |
| 2005/0033132 | A1 * | 2/2005 | Shults | A61L 31/10 604/890.1 |
| 2006/0023397 | A1 * | 2/2006 | Brendel | H01G 4/35 361/302 |
| 2006/0145353 | A1 | 7/2006 | Kirby et al. | |
| 2007/0150036 | A1 * | 6/2007 | Anderson | A61N 1/0551 607/116 |
| 2007/0197889 | A1 * | 8/2007 | Brister | A61B 5/1495 600/347 |
| 2009/0215296 | A1 * | 8/2009 | Chambers | A61N 1/3752 439/271 |
| 2009/0270765 | A1 * | 10/2009 | Ghesquiere | A61B 5/15113 600/583 |
| 2010/0030045 | A1 * | 2/2010 | Gottlieb | A61B 5/1473 600/347 |
| 2010/0094364 | A1 * | 4/2010 | McDonald | H01R 43/00 607/2 |
| 2011/0021889 | A1 * | 1/2011 | Hoss | A61B 5/14865 600/310 |
| 2011/0021943 | A1 * | 1/2011 | Lacour | A61N 1/0551 607/118 |
| 2011/0121850 | A1 * | 5/2011 | Lee | G01R 1/06722 324/756.02 |
| 2011/0230735 | A1 * | 9/2011 | Wolfe | A61B 5/14503 204/403.14 |
| 2012/0265042 | A1 * | 10/2012 | Neinast | A61B 5/6849 600/347 |
| 2012/0315798 | A1 | 12/2012 | Poon et al. | |
| 2013/0144369 | A1 * | 6/2013 | Elias | A61B 5/6877 607/116 |
| 2013/0184796 | A1 | 7/2013 | Marzano et al. | |
| 2013/0184797 | A1 * | 7/2013 | Tang | H02G 3/22 607/116 |
| 2013/0256125 | A1 | 10/2013 | Young et al. | |
| 2013/0288501 | A1 | 10/2013 | Russell et al. | |

(56) References Cited

U.S. PATENT DOCUMENTS

| | | | |
|---|---|---|---|
| 2014/0135605 A1* | 5/2014 | Gottlieb | A61B 5/1486 |
| | | | 600/347 |
| 2014/0277266 A1* | 9/2014 | Khalil | A61N 1/36178 |
| | | | 607/46 |
| 2014/0277317 A1 | 9/2014 | Tooker et al. | |
| 2014/0347839 A1 | 11/2014 | Shah et al. | |
| 2014/0378993 A1 | 12/2014 | Shah et al. | |
| 2015/0051677 A1* | 2/2015 | Marnfeldt | A61N 1/3752 |
| | | | 607/116 |
| 2015/0157853 A1 | 6/2015 | Verzal et al. | |
| 2015/0174415 A1* | 6/2015 | Angara | H02J 7/025 |
| | | | 607/46 |
| 2015/0180271 A1* | 6/2015 | Angara | H02J 50/12 |
| | | | 607/46 |
| 2016/0015977 A1* | 1/2016 | Biele | A61N 1/36125 |
| | | | 607/46 |
| 2016/0030753 A1 | 2/2016 | Shah et al. | |
| 2016/0263384 A1* | 9/2016 | Stevenson | H01G 4/12 |
| 2016/0380381 A1 | 12/2016 | Shah et al. | |
| 2018/0169417 A1 | 6/2018 | Urbanski et al. | |
| 2018/0277970 A1* | 9/2018 | Shah | H05K 1/02 |
| 2018/0345023 A1 | 12/2018 | Shah et al. | |

FOREIGN PATENT DOCUMENTS

| | | | | |
|---|---|---|---|---|
| DE | 102008045819 B4 * | 9/2015 | ............... | H01B 3/46 |
| EP | 0811397 | 12/1997 | | |
| EP | 2140909 A1 * | 1/2010 | ........... | A61N 1/3752 |
| KR | 20160000683 A * | 1/2016 | | |
| WO | WO-9002581 A1 * | 3/1990 | ............. | H01R 13/41 |
| WO | WO-2008025159 A1 * | 3/2008 | ............. | A61N 1/375 |
| WO | WO-2010007580 A1 * | 1/2010 | ........ | A61B 5/14532 |
| WO | 2013142734 | 9/2013 | | |
| WO | WO-2016044042 A1 * | 3/2016 | ............. | H01R 12/71 |
| WO | WO-2020072941 A1 * | 4/2020 | ............. | A61N 1/048 |

OTHER PUBLICATIONS

U.S. Appl. No. 15/923,490 , "Notice of Allowance", dated Nov. 14, 2019, 10 pages.

BalSeal , "BalSeal Engineering, Inc.", SYGNUS Implantable COntact System, Integrated seal/contact system for active medical implantables (http://sygnus.com/pdfs/SYGNUS-TMB10.pdf), Copyright 2012.

International Application No. PCT/US2018/023143 , "International Preliminary Report on Patentability", dated Oct. 3, 2019, 8 pages.

International Application No. PCT/US2018/023143 , "International Search Report and Written Opinion", dated Jul. 6, 2018, 11 pages.

* cited by examiner

IMPLANTABLE CONNECTOR INCLUDING AT LEAST ONE ELECTRICAL COMPONENT

CROSS-REFERENCE TO RELATED APPLICATIONS

The present application is a continuation of U.S. patent application Ser. No. 15/923,490, filed on Mar. 16, 2018, which claims priority to U.S. Provisional Application No. 62/475,365, filed on Mar. 23, 2017, and entitled "Implantable Connector," the entirety of each of which are hereby incorporated by reference herein.

BACKGROUND

Implantable medical devices can be used for monitoring (e.g., ongoing glucose monitoring) and for stimulation (e.g., to regulate the beating of a heart). An example device can include an electronics package connected to one or more leads via a connector. The one or more leads can be placed at a target location for monitoring or stimulation. In a monitoring scenario, the leads gather information from the target location and the electronics package processes the information. In a stimulation scenario, the electronics package generates electrical signals that are delivered to the target location via the leads.

SUMMARY

Various examples are described relating to implantable connectors, systems including the implantable connectors, methods for using the implantable connectors, and methods for forming the implantable connectors.

In an example, a device is described. The device includes a first component, a second component, a compressible electrical contact, and a compressible gasket. The first component includes an interconnect board include a first board surface and a second board surface, a first conductive conduit extending between a first bond pad on the first board surface and a second bond pad on the second board surface, and an electric lead electrically connected to the first conductive conduit via the first bond pad. The second component includes a feedthrough substrate including a first substrate surface and a second substrate surface, a second conductive conduit extending between a third bond pad on the first substrate surface and a fourth bond pad on the second substrate surface, an electronic device electrically connected to the second conductive conduit via the third bond pad, and a housing under which is disposed the electronic device and the first substrate surface. The compressible electrical contact is attached to at least one of the second bond pad or the fourth bond pad. The compressible gasket is attached to at least one of the interconnect board or the feedthrough substrate. The compressible gasket extends about the compressible electrical contact. In some examples, when the first component and the second component are mechanically coupled, the compressible electrical contact is compressed so as to electrically connect the first conductive conduit and the second conductive conduit.

In another example, a device is described. The device includes a planar board including a first set of conductive pathways extending between a first side of the planar board and a second side of the planar board. The device also includes first electrical contacts disposed on the first side of the planar board. The device also includes a first set of bond pads disposed on the second side of the planar board. The first set of bond pads is electrically connected to the first electrical contacts via the first set of conductive pathways. The device also includes a planar substrate including a second set of conductive pathways extending between a first side of the planar substrate and a second side of the planar substrate. The device also includes second electrical contacts disposed on the first side of the planar substrate. The device also includes a second set of bond pads disposed on the second side of the planar substrate. The second set of bond pads is electrically connected to the second electrical contacts. The device also includes a set of compressible electrical contacts extending between the first set of bond pads and the second set of bond pads. The device also includes a mechanical coupler extending between the planar board and the planar substrate. The mechanical coupler is configured to couple the planar board and the planar substrate. The set of compressible electrical contacts is held in compression by the mechanical coupler so as to electrically connect the first electrical contacts and the second electrical contacts.

In yet another example, a system is described. The system includes an electronics package, a neural interface, and a mechanical coupler. The electronics package includes a feedthrough substrate including a first substrate surface and a second substrate surface, a plurality of conductive conduits extending between the first substrate surface and the second substrate surface, a first plurality of bond pads disposed on the second substrate surface, an electronic device electrically connected to the first plurality of bond pads via the plurality of conductive conduits, and a housing enclosing the electronic device and the second substrate surface. The neural interface includes an interconnect board including a first board surface and a second board surface, a plurality of electrical leads attached to the first board surface, a second plurality of bond pads disposed on the second board surface, a plurality of compressible contacts attached to the second plurality of bond pads, and a compressible gasket attached to the second board surface. The compressible contact physically separates and electrically isolates individual ones of the plurality of compressible contacts. The second plurality of bond pads is electrically connected to the plurality of electrical leads. The mechanical coupler is configured to mechanically couple the neural interface and the electronics package so as to hold the plurality of compressible contacts in physical contact with the first plurality of bond pads.

In yet another example, a method is described. The method includes implanting a set of electrodes of a neural interface at an incision location. The neural interface includes a planar board including a first board side and a second board side, and a set of conductive conduits extending through the planar board so as to electrically connect a set of compressible electrical contacts disposed on the first board side and the set of electrodes disposed on the second board side. The method also includes aligning the set of compressible electrical contacts with a corresponding set of bond pads of an electronics package. The method also includes coupling the neural interface and the electronics package to form a coupled package.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of implantable connectors for use in neurostimulation devices. Those of ordinary skill in the art will realize that the following description is illustrative only and is not intended to be in any way limiting. For example, the implantable connectors described herein can also be used for monitoring devices. In some examples, the implantable connectors can be used in applications that are not implanted in human tissue. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, an implantable connector includes two separate components, an electronics package and a neural interface, that together form the implantable connector. The neural interface includes a planar body at which is bonded a set of electrodes. The electrodes are placed at target location(s) in a person's body. The neural interface also includes a set of spring contacts arranged in a two-dimensional array and a compressible gasket. The set of springs are electrically connected to the set of electrodes by way of conductive conduits extending through the planar body. The electronics package includes electronics (e.g., application-specific integrated circuit (ASIC), power supply, printed circuit board, antennas, etc.) supported by a planar substrate. On the opposite side of the planar substrate, the electronics package includes a set of exposed bond pads arranged in a two-dimensional array that matches the array of the set of spring contacts. The exposed bond pads are electrically connected to the electronic devices by way of conductive conduits extending through the planar substrate.

To connect the electronics package and the neural interface, the spring contacts and the exposed bond pads are aligned and a mechanical coupler, which is part of the implantable connector, is used to compress the spring contacts into contact with the exposed bond pads. This action also compresses the compressible gasket which electrically isolates and physically separates the set of spring contacts from each other. The implantable connector can also include a housing that encloses the electronics package. In some examples, the structure of the housing is the mechanical coupler. In other examples, the mechanical coupler is separate and includes screws, clamps, or other mechanical means to hold the spring contacts and the compressible gasket in compression.

This illustrative example is given to introduce the reader to the general subject matter discussed herein and the disclosure is not limited to this example. The following sections describe various additional non-limiting examples of implantable connectors.

Figure 1:
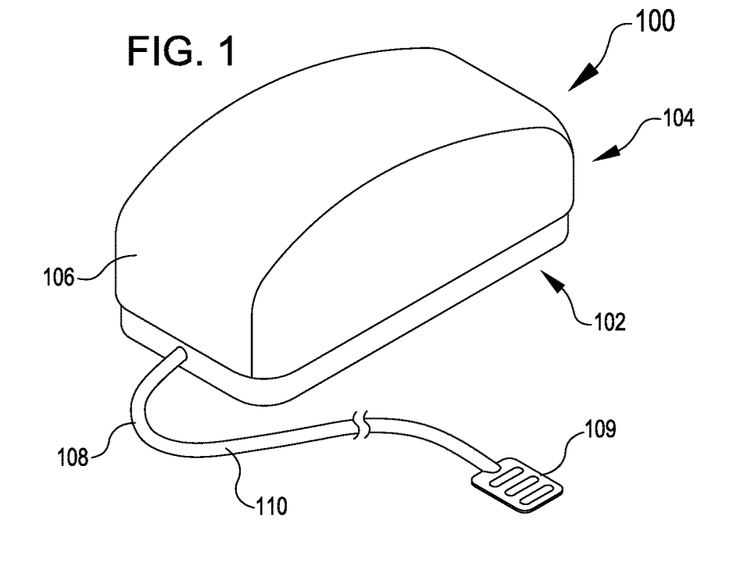
FIG. 1 illustrates a perspective view of an implantable connector, according to at least one example.

Referring now to FIG. 1, FIG. 1 illustrates an implantable connector 100, according to at least one example. The implantable connector 100 includes a neural interface 102 and an electronics package 104. In FIG. 1, the neural interface 102 and the electronics package 104 are illustrated in a connected state. Components of the electronics package 104 are disposed within a housing 106 of the implantable connector 100.

The neural interface 102 includes a set of electrodes 108. A portion of the set of electrodes 108 is carried within a flexible cable 110 and exposed at a distal end 109. The distal ends 109 of the electrodes 108 can be placed at one or many target locations, depending on the implementation. In some examples, each electrode 108 is included in its own flexible cable 110. In some examples, multiple electrodes 108 are included in the same flexible cable 110. The diameters of the electrodes 108 can vary depending on the application.

The implantable connector 100 can be used in connection with any suitable active implantable device such as those for neuromodulation, neurostimulation, and/or monitoring. Examples of such devices include deep brain stimulators, cochlear implants, cardiac pacemakers, bioelectric devices, and other similar devices. The implantable connector 100 can also be used for sensing and delivery devices such as glucose monitoring and delivery systems.

In FIG. 1, the implantable connector 100 is illustrated as providing a connection between an active component (e.g., the electronics package 104) and a passive component (e.g., the neural interface). In some examples, the implantable connector 100 is used to provide a connection between two passive components (e.g., as a lead extension) or two active components.

In some examples, the neural interface 102 along with the electrodes 108 are implanted in a person's body through one or more incisions. As part of the same surgery, the electronics package 104 is connected to the neural interface 102 and both are implanted. If, after a time, the electronics package 104 wears out or otherwise needs replacing, the electronics package 104 can be easily unconnected from the neural interface 102. After which, a new electronics package 104 can be installed in place of the now-removed electronics package 104. As the neural interface 102 is built as a passive component, it may remain in the person's body without need of replacing.

Figure 2:
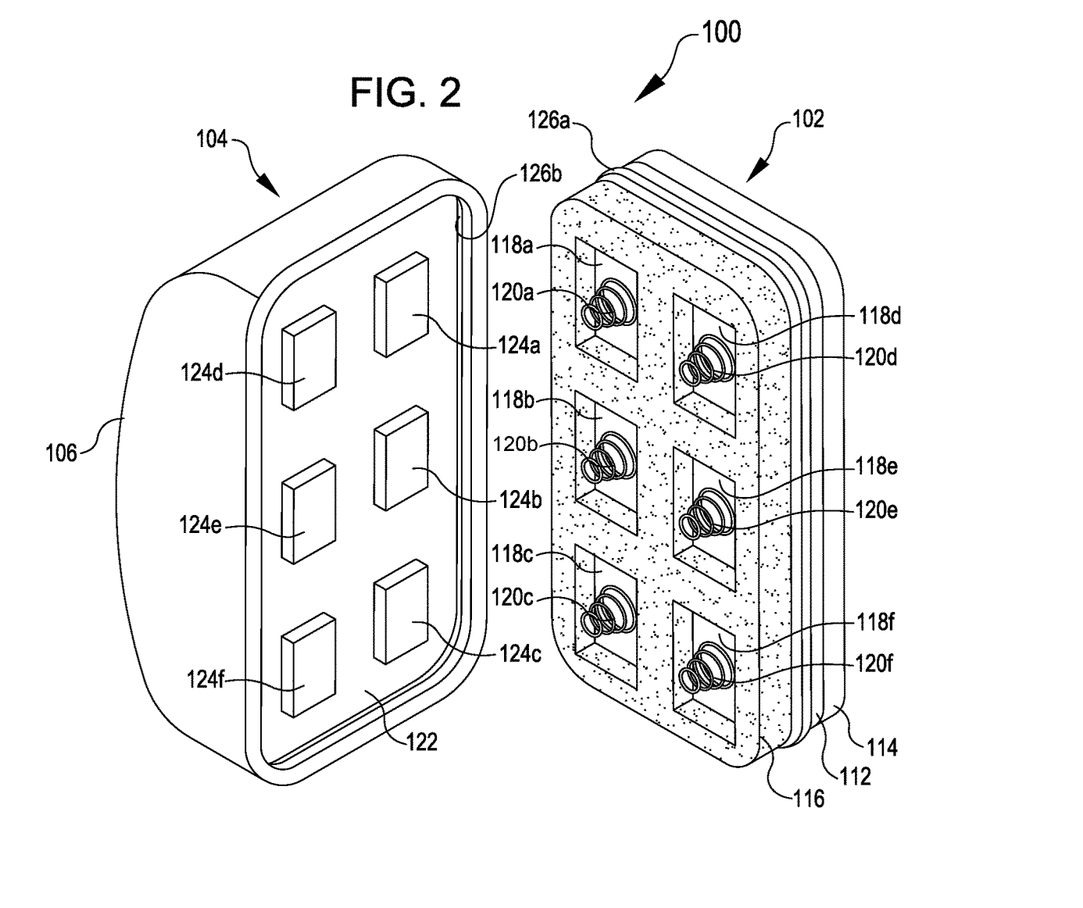
FIG. 2 illustrates a perspective view of a pair of components of the implantable connector of FIG. 1, according to at least one example.

FIG. 2 illustrates a perspective view of the neural interface 102 and the electronics package 104 the implantable connector 100, according to at least one example. In FIG. 2, the neural interface 102 and the electronics package 104 are illustrated in a disconnected state. The neural interface 102 includes an interconnect board 112 disposed between an insulative layer 114 and a compressible gasket 116. The interconnect board 112 can be defined as having two planar surfaces opposite each other.

As described in detail herein, the electrodes 108 are embedded within the insulative layer 114 and attached to the interconnect board 112. On an opposite side of the interconnect board 112, is attached a set of bond pads 118a-118f. The bond pads 118 are illustrated in a two-dimensional array (e.g., 2×3). In some examples, any suitable number of bond pads 118 can be attached to the interconnect board 112 (e.g., 1-100 or more), which may be held in a suitable one-dimensional array, two-dimensional array, or other suitable pattern. For example, an example implantable connector 100 having a circular aspect ratio may include an example neural interface 102 that includes a circular array of bond pads 118.

The neural interface 102 also includes a set of compressible contacts 120a-f ("the compressible contacts 120") attached to the bond pads 118. In FIG. 1, the compressible contacts 120 are illustrated as coil springs. In some examples, each compressible contact 120 can be any suitable structure or device capable of conducting electricity and compressing (e.g., different varieties of springs, telescoping pogo pins, and other similar structures). In some examples, the compressible contacts 120 are formed from a conductive material that has properties of low creep, elastic deformation, and is chemically inert. Such properties may be desirable given that the compressible contacts 120, in some examples, are compressed for very long periods of time (e.g., years, decades, or even longer). Additionally, forming the compressible contacts 120 from a chemically inert material ensures that the compressible contacts 120 are suitable for long term implantation. For example, the compressible contacts 120 can be formed from titanium, platinum, platinum-iridium alloy, nitinol (e.g., nickel-titanium alloy), niobium, gold, or any other biocompatible metal or alloy.

In some examples, each compressible contact 120 is defined by a compression axis. Each compressible contact 120 can be compressible in a first direction along the compression axis and extendable in a second direction along the compression axis. The second direction can be opposite the first direction.

In some examples, a pitch value measured between the compressible contacts 120 is between 0.5 millimeters and 2 millimeters. For example, a pitch value between a first compressible contact 120a and a second compressible contact 120b and/or between the first compressible contact 120a and a third compressible contact 120d is between 0.5 millimeters and 2 millimeters. Thus, in some examples, the pitch value may be uniform. In other examples, the pitch value is non-uniform. Depending on the implementation, the pitch value may be less than 0.5 millimeters (e.g., 0.1 millimeters) or greater than 2 millimeters.

The insulative layer 114 can be formed from an insulative material such as epoxy and may function to insulate connections between the electrodes 108 and the interconnect board 112.

The compressible gasket 116 can be formed from silicone and/or other materials having similar properties. In some examples, the compressible gasket 116 is formed from a medical grade silicone such as long-term implantable silicone. In some examples, short term implantable silicone may also be used. The compressible gasket 116, which is placed in compression when the electronics package 104 and the neural interface 102 are connected, functions to physically separate and electrically isolate the compressible contacts 120. Thus, the compressible gasket 116 can include openings through which the compressible contacts 120 extend. In some examples, the compressible gasket 116 includes a set of compressible gaskets 116 corresponding to each of the compressible contacts 120. Thus, the ratio of compressible gaskets 116 to compressible contacts 120 can be 1:1. The compressible gasket 116 provides at least an ionic barrier between the compressible contacts 120 and an environment in which the implantable connector 100 is implanted. In some examples, the compressible gasket 116 provides a hermetic barrier between the compressible contacts 120 and the environment. In some examples, the compressible gasket 116 can be attached to a feedthrough substrate 122 of the electronics package 104 or may be a separate component that is held in place by compression (e.g., is not attached to either the feedthrough substrate 122 or the interconnect board 112).

In some examples, a layer of an insulating material is applied over the top of the bond pads 118 and the compressible contacts 120. The layer may be sufficiently thin such that the compressible contacts 120 can extend through the layer. This layer of insulating material may provide additional electrical isolation of the compressible contacts 120.

Turning now the electronics package 104, as illustrated in FIG. 2, the electronics package 104 includes the feedthrough substrate 122 and the housing 106. The feedthrough substrate 122 functions to support electronics held within the housing 106. The feedthrough substrate 122 can be defined as having two planar surfaces opposite each other. The feedthrough substrate 122 also includes a set of bond pads 124a-124f. The bond pads 124 are illustrated in a two-dimensional array (e.g., 2×3). In some examples, any suitable number of bond pads 124 can be attached to the feedthrough substrate 122 (e.g., 1-100 or more), which may be held in any suitable one-dimensional array, two-dimensional array, or other suitable pattern. The number and arrangement of the bond pads 124 can match the number and arrangement of the compressible contacts 120. In some examples, the compressible contacts 120 are attached to the feedthrough substrate 122 (e.g., at the bond pads 124 instead of the bond pads 118).

In the connected state illustrated in FIG. 1, the compressible contacts 120 are in physical contact with the bond pads 124 and held in a manner that compresses the compressible contacts 120. In this manner, multiple independent electrical connections can be formed between the electronics package 104 and the neural interface 102.

The implantable connector 100 also includes a mechanical coupler 126. Generally, the mechanical coupler 126 can be any suitable structure configured to hold the electronics package 104 and the neural interface 102 in physical contact. In particular, the mechanical coupler 126 is configured to hold the compressible contacts 120 and the compressible gasket 116 in compression respectively with the bond pads 124 and the feedthrough substrate 122. To this end, the mechanical coupler 126 can include a set of screws, a set of clamps, a set of clips, or other suitable structures. The mechanical coupler 126 can be designed to maintain a certain degree of planarity between the interconnect board 112 and the feedthrough substrate 122. This may ensure that all of the compressible contacts 120 are equally compressed. In some examples, the interconnect board 112 can include alignment tabs or other geometrical alignment features attached thereto (e.g., at the corners, the middle, the edges, etc.) and extending in the same direction as the compressible contacts 120 a fixed amount (e.g., have a fixed height). The housing 106 and/or the feedthrough substrate 122 can include alignment tabs or other alignment features corresponding to the alignment features from the interconnect board 112. These alignment features may also have a fixed height. As the mechanical coupler 126 is used to couple the electronics package 104 and the neural interface 102, the alignment features or other structures are aligned and function as physical barriers to keep a proper alignment between the electronics package 104 and the neural interface 102. Such alignment features may be used with examples of the mechanical coupler 126 that are variable in nature (e.g., screws, adjustable clamps, etc.). In some examples, the alignment features function to ensure that the compressible contacts 120 can only be compressed to a known maximum compression state. For example, the electronics package 104 may include a set of tabs that are shorter than the compressible contacts 120, but come into contact with the neural interface 102 when the proper compression state of the compressible contacts 120 is achieved.

In some examples, the alignment features provide passive alignment during installation of the electronics package 104 and the neural interface 102. The alignment features may be configured such that the electronics package 104 and the neural interface 102 can only be brought together in one specific orientation. This may prevent inadvertent rotation of the electronics package 104 with respect to the neural interface 102.

In some examples, an offset value measured between the bond pads 118 and the bond pads 124 is between 0.1 millimeters and 2 millimeters. To achieve planarity between the feedthrough substrate 122 and the interconnect board 112, the offset value measured at any one of the bond pad locations should be within some threshold (e.g., 1-5% of an expected value). Thus, uniformity in the offset value may be an indication of planarity of the system.

In FIG. 2, an example of a fixed distance mechanical coupler 126 is illustrated. In this example, the mechanical coupler 126 is essentially disposed between the housing 106 and the interconnect board 112. In particular, the mechanical coupler 126 can include a ridge 126a on the interconnect board 112 and a lip 126b on the housing 106. The ridge 126a extends around an exterior edge of the interconnect board 112. The lip 126b extends around an interior surface of the housing 106. The size of shape of the ridge 126a and the lip 126b can be selected to correspond to each other. For example, the ridge 126a may be sized slightly smaller than the lip 126b such that bringing the ridge 126a and the lip 126b into contact creates a "snap-fit" between the two components. In some examples, the mechanical coupler 126 holds the electronics package 104 and the neural interface 102 together such that the compressible contacts 120 are held in compression against the bond pads 124. Because of this, electrical connections are formed between the electrodes 108 and components of the electronics package 104.

A connecting force required to connect the neural interface 102 and the electronics package 104 can be very low compared to other connectors that form a similar connection by plugging a circular lead into a header including circular springs and silicone gaskets. This may be because of the planar disposition of the compressible contacts 120 and the bond pads 124, and the use of the mechanical coupler 126.

Figure 3:
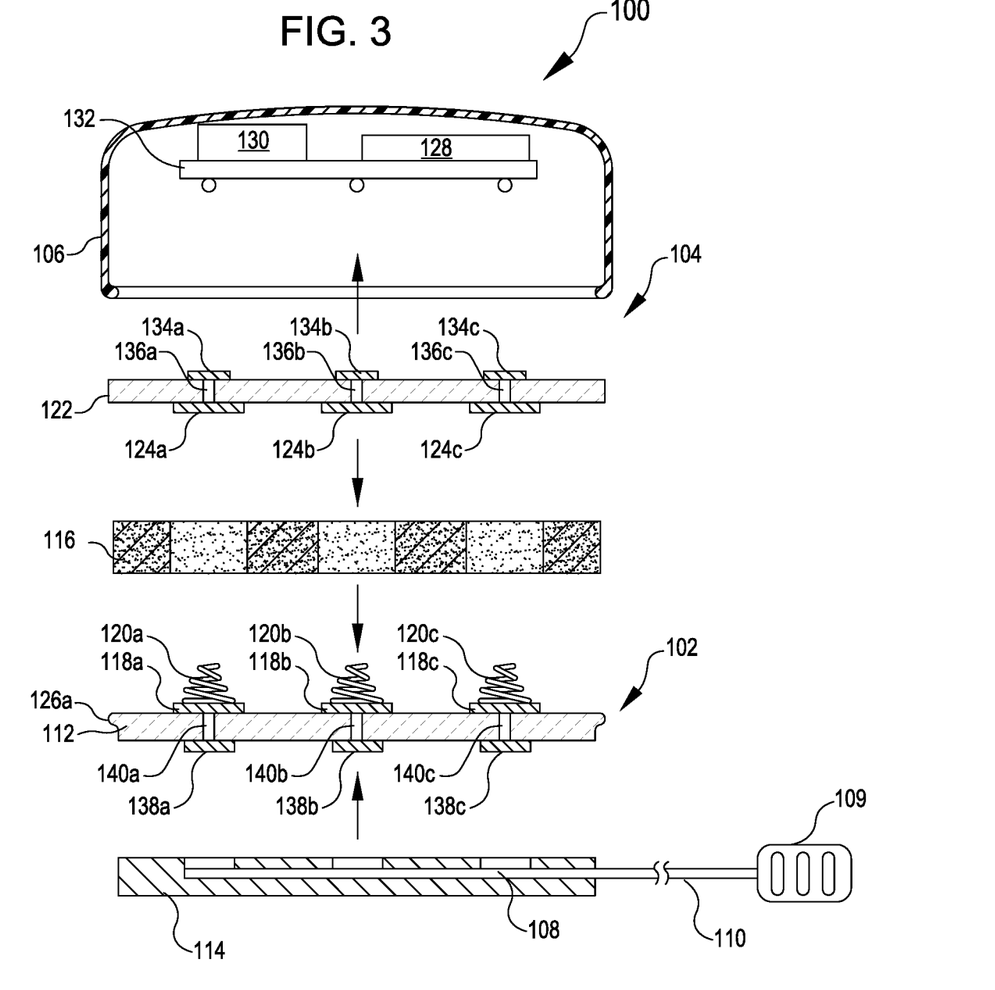
FIG. 3 illustrates an exploded view of the implantable connector of FIG. 1, according to at least one example.

FIG. 3 illustrates an exploded view of the implantable connector 100, according to at least one example. The electronics package 104 of the implantable connector 100 can include any suitable electronic component or device to enable sensing, monitoring, and stimulation of human systems. Such componentry includes, in some examples, an ASIC 128 and a power supply 130, which can be attached to a circuit board 132. The ASIC 128 and/or the circuit board 132 can also include other electronic components or devices such as antennas, transceivers, inductive coils, recording devices, memory, and any other suitable components to enable sensing, monitoring, and stimulation of human systems. The ASIC 128, the power supply 130, and the circuit board 132 can be housed within the housing 106. In some examples, a hermetic seal is formed between the housing 106 and the feedthrough substrate 122. For example, the seal can be formed between an interior surface of the housing 106 and an exterior surface of the feedthrough substrate 122.

The feedthrough substrate 122 can be formed from ceramic or other material having insulative properties. In some examples, the feedthrough substrate 122 is a printed circuit board. The circuit board 132, which can be a printed circuit board, can be attached to the feedthrough substrate 122 via a set of bond pads 134a-c formed on a surface of the feedthrough substrate 122. In some examples, the connection between the circuit board 132 and the feedthrough substrate 122 is formed using other conventional connecting techniques. The bond pads 134a-c and/or 124 can be deposited using thin-film deposition (e.g., physical vapor deposition, chemical vapor deposition, atomic layer deposition, etc.) or by printing a thick-film paste of metal that is fired at an elevated temperature.

The feedthrough substrate 122 includes a set of conductive conduits 136a-c that extend between the bond pads 134a-c and the bond pads 124. In some examples, the feedthrough substrate 122 includes multi-layer routing to provide different designs of the conductive conduits 136a-c other than those illustrated. The conductive conduits 136a-c can be considered vias, electrical traces, and/or any combination of the foregoing.

In some examples, the electronics package 104 and the neural interface 102 are manufactured as separate components and connected during implantation. For example, the electronics package 104, extending between the housing 106 and the bond pads 124, can be formed as part of a first manufacturing process. As part of a second manufacturing process, the neural interface 102 can be formed. Once both the first and the second manufacturing processes are complete, the electronics package 104 and the neural interface 102 can be brought together.

The interconnect board 112 can be fabricated using co-fired ceramics with metallization on both sides of the interconnect board 112 or on one side of the interconnect board 112. The electrodes 108 can be bonded to interconnect board 112 via a set of bond pads 138a-c. The bond pads 138a-c are electrically connected to the bond pads 118 via a set of conductive conduits 140a-c. In this manner, the electrodes 108 of the neural interface 102 are electrically connected to the compressible contacts 120. The conductive conduits 140a-c can be considered vias, electrical traces, and/or any combination of the foregoing.

The compressible contacts 120 can be fabricated using coiling or some other suitable technique. The compressible contacts 120 can be attached to the bond pads 118 using laser welding, resistance welding, brazing, or any other suitable attachment technique. In some examples, the material selected for the compressible contacts 120 is the same material as selected for the bond pads 118, and/or the bond pads 124.

The compressible gasket 116 can be formed as a separate part and attached to the interconnect board 112. In some examples, the compressible gasket 116 is formed directly on the interconnect board 112. Techniques to form the compressible gasket 116 include, for example, molding, laser cutting, die cutting, and other similar techniques. The compressible gasket 116 can be formed from any suitable compressible material such as silicon. In some examples, the silicone selected is curable using ultraviolet light.

The insulative layer 114 can be formed using any suitable technique and may function to insulate the connections between the electrodes 108 and the bond pads 138a-c. For example, the insulative layer 114 can be formed from an epoxy that is molded over the interconnect board 112. In some examples, the insulative layer 114 and the compressible gasket 116 are formed from the same material. In some examples, the insulative layer 114 and the compressible gasket 116 are formed as the same part.

Figure 4:
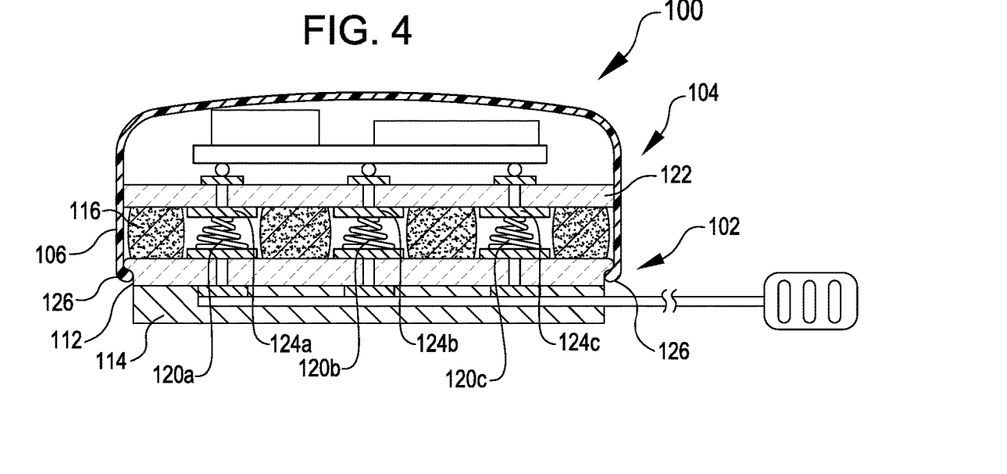
FIG. 4 illustrates a profile view of the implantable connector of FIG. 1, according to at least one example.

FIG. 4 illustrates a profile view of the implantable connector 100, according to at least one example. In FIG. 4, the implantable connector 100 is illustrated in connected state (e.g., after the neural interface 102 and the electronics package 104 have been connected). To assemble the implantable connector 100, the compressible contacts 120 are aligned with the bond pads 124. Once aligned, the compressible contacts 120 and/or the bond pads 124 are moved towards each other (e.g., a connecting force is applied to the electronics package 104 in the direction that compresses the compressible contacts 120). Once distal portions of the compressible contacts 120 contact the bond pads 124, the connecting force compresses the compressible contacts 120. This causes electrical connections to be formed between the compressible contacts 120 and the bond pads 124. The connecting force also causes the compressible gasket 116 to compress between the feedthrough substrate 122 and the interconnect board 112.

In some examples, the connecting force is applied by a human user such as a surgeon who is implanting the implantable connector 100. Once the force has been applied, the mechanical coupler 126 is used to retain the two components (e.g., the neural interface 102 and the electronics package 104) together.

In some examples, the connecting force is applied as the human user utilizes the mechanical coupler 126 to couple the neural interface 102 and the electronics package 104. For example, the mechanical coupler 126 can include one or more screws extending between the interconnect board 112 and the feedthrough substrate 122. As the human user tightens the screws, a distance between the interconnect board 112 and the feedthrough substrate 122 is reduced, which causes the compressible contacts 120 to compress against the bond pads 124 and the compressible gasket 116 to compress against the feedthrough substrate 122. A similar procedure is completed when the mechanical coupler 126 includes a set of clamps.

In any event, the mechanical coupler 126 can be configured to hold the compressible contacts 120 in physical contact with the bond pads 124. This ensures that a suitable electrical connections between the neural interface 102 and the electronics package 104 are achieved.

In some examples, at least two of the compressible contacts 120 are electrically connected to each other and not connected to the electrodes 108. Once the implantable connector 100 is properly assembled, electrical continuity in the implantable connector 100 can be verified based on an electrical circuit being formed between the two compressible contacts 120.

In some examples, the ASIC 128 or other electronic device includes a feature that allows a user to verify that electrical continuity has been achieved between the electronics package 104 and the neural interface 102. For example, the feature may rely on feedback that the two compressible contacts 120 described above are shorted together. In some examples, this feature tests other connections formed by other compressible contacts 120 that are connected to the electrodes 108. This feature may be beneficial to ensure that the compressible contacts 120 are sufficiently compressed so as to form the independent connections between the electronics package 104 and the neural interface 102.

Figure 5:
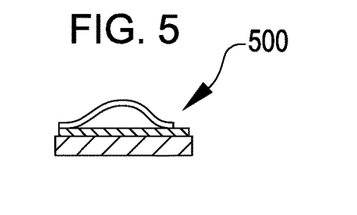
FIG. 5 illustrates an example compressible electrical contact, according to at least one example.

FIG. 5 illustrates an example compressible contact 500, according to at least one example. The compressible contact 500 is an example of the compressible contact 120 described herein. The compressible contact 500 is an example of a leaf spring contact. In some examples, the compressible contact 500 undergoes elastic deformation under the connecting force.

Figure 6:
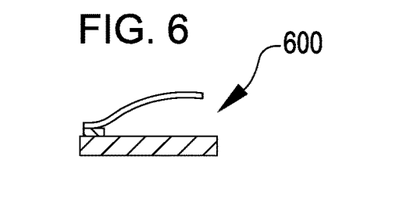
FIG. 6 illustrates an example compressible electrical contact, according to at least one example.

FIG. 6 illustrates an example compressible contact 600, according to at least one example. The compressible contact 600 is an example of the compressible contact 120 and the compressible contact 500 described herein. The compressible contact 600 is an example of a cantilever spring. In some examples, the compressible contact 600 undergoes elastic deformation under the connecting force.

Figure 7:
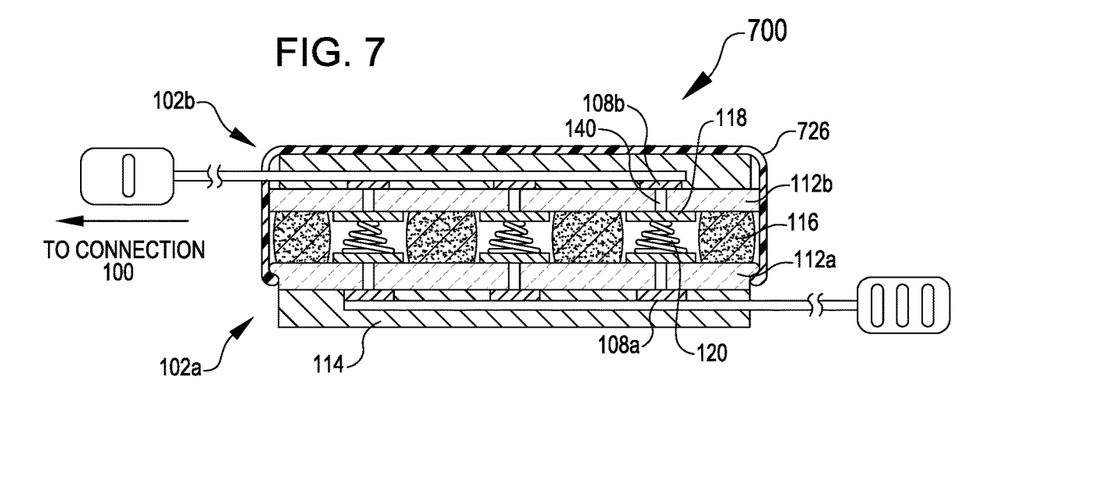
FIG. 7 illustrates an example implantable connector, according to at least one example.

FIG. 7 illustrates an example implantable connector 700, according to at least one example. The implantable connector 700 is an example of a connection that can be made between two passive components (e.g., two neural interfaces 102a, 102b). For example, the implantable connector 700 can be used to extend a first neural interface 102a by a length of a second neural interface 102b. In some examples, the second neural interface 102b simply includes a set of electrodes 108b that are connected to the electrodes 108a of the first neural interface 102a by means of the compressible contacts 120 and the interconnect board 112a.

The second neural interface 102b can include an interconnect board 112b and a set of bond pads 118. The set of bond pads 118 are electrically connected to the electrodes 108b via conductive conduits 140a-c.

The implantable connector 700 also includes a mechanical coupler 726. In this example, the mechanical coupler 726 functions to couple the two neural interfaces 102a, 102b together. This coupling holds the compressible contacts 120 of the first neural interface 102a with the bond pads 118 of the second neural interface 102b.

Figure 8:
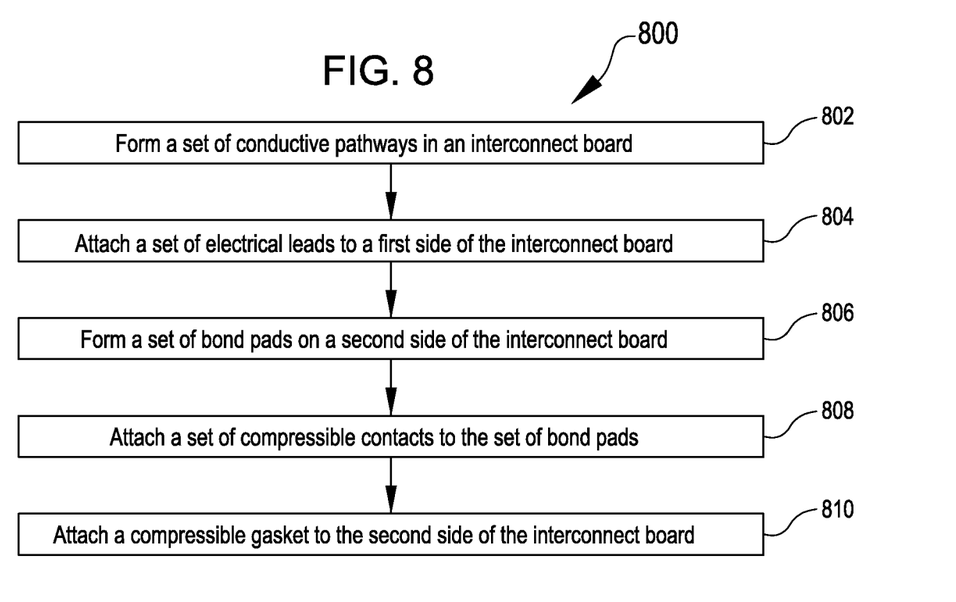
FIG. 8 illustrates an example flow process of manufacturing an implantable connector, according to at least one example.

FIG. 8 illustrates an example process 800 of manufacturing an implantable connector, according to at least one example.

The process 800 begins at 802 by forming a set of conductive pathways in an interconnect board. In some examples, the interconnect board is a printed circuit board and the set of conductive pathways are electrical traces that extend between opposite sides of the printed circuit board. In this example, the electrical traces can be plated vias.

At 804, the process 800 includes attaching a set of electrical leads to a first side of the interconnect board. In some examples, the electrical leads are attached so as to electrically connect the set of conductive pathways and the set of electrical leads. The set of electrical leads can correspond to a set of electrodes of a neural interface. Attaching the set of electrical leads can include bonding the set of electrical leads to a set of bond pads electrically coupled to the set of conductive pathways.

At 806, the process 800 includes forming a set of bond pads on a second side of the interconnect board. In some examples, the set of bond pads are electrically connected to the set of conductive pathways. The set of bond pads can be deposited on the second side or formed in any other suitable manner.

At 808, the process 800 includes attaching a set of compressible contacts to the set of bond pads. The set of compressible contacts can be formed in any suitable manner. The set of compressible contacts can be attached to the set of bond pads using laser welding, resistance welding, brazing, or any other suitable attachment technique.

At 810, the process 800 includes attaching a compressible gasket to the second side of the interconnect board. In some examples, the set of compressible contacts extend through respective openings of the compressible gasket. The compressible gasket can be glued to the interconnect board or attached in any other suitable manner.

In some examples, the process 800 further includes providing an electronics package that includes a set of exposed bond pads. In some examples, the process 800 further includes coupling, via a mechanical coupler, the electronics package and the interconnect board such that the set of exposed bond pads physically contact the set of compressible contacts and the compressible gasket physically contacts the electronics package. In some examples, coupling via the mechanical coupler, includes releasably coupling the electronics package and the interconnect board. In this manner, the electronics package can be removed from the interconnect board at a later time (e.g., when the electronics package wears out).

Figure 9:
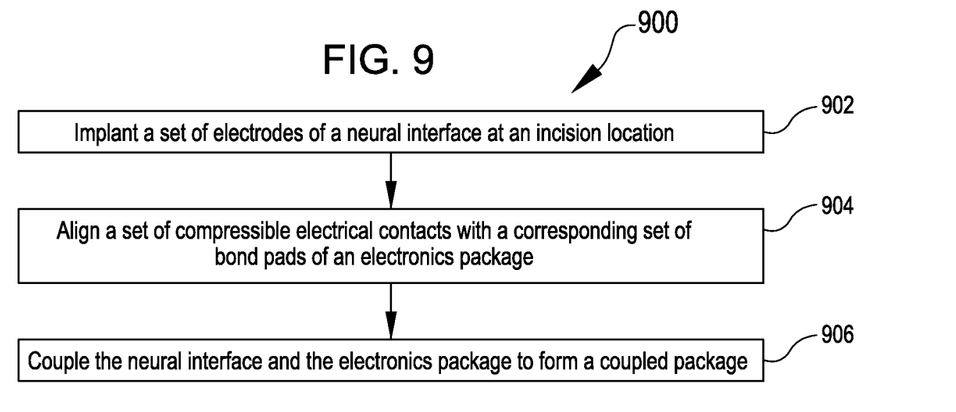
FIG. 9 illustrates an example process of using an implantable connector, according to at least one example.

FIG. 9 illustrates an example process of using an implantable connector, according to at least one example.

The process 900 begins at 902 implanting a set of electrodes of a neural interface at an incision location. This may be performed by a human operator or an automated operator such as a robotic manipulator. The neural interface can include a planar board and a set of conductive conduits extending through the planar board. The planar board can be defined as having a first board side and a second board side. The set of conductive conduits can extend through the board. The set of conductive conduits electrically connect a set of compressible electrical contacts disposed on the first board side and the set of electrodes disposed on the second board side.

At 904, the process 900 includes aligning the set of compressible electrical contacts with a corresponding set of bond pads of an electronics package. This may be achieved using one or more alignment structures of the neural interface and/or the electronics package. The electronics package includes a planar substrate including a first planar side and a second planar side, electronic devices supported by the first planar side, a housing coupled to the planar substrate so as to enclose the electronic devices, and a second set of conductive conduits extending between first planar side and the second planar side. In some examples, the corresponding set of bond pads is electrically connected to the electronic devices via the second set of conductive conduits.

At 906, the process 900 includes coupling the neural interface and the electronics package to form a coupled package. This may be achieved using a mechanical coupler that couples the neural interface and the electronics package. For example, the mechanical coupler can be integrated into a housing of the electronics package that engages with a corresponding structure of the neural interface. In some examples, the mechanical coupler includes a set of clamps that extend between the neural interface and the electronics package. In this example, coupling the neural interface and the electronics package includes the operator articulating the clamps to a clamped state. The mechanical coupler can be configured to hold the neural interface and the electronics package.

In some examples, the process 900 further includes placing the coupled package at the incision location or at a different incision location. This can include placing the coupled package subcutaneously at the incision location or at the different incision location. In some examples, the coupled package is placed outside of the skin. For example, the process 900 can be performed to create a temporary connection between the electronics package and the neural interface. Assume it is unknown which of a variety of different electronics packages (or which settings) is suitable for a patient. In this example, the electrodes of the neural interface can be placed under the skin. Because the neural interface is modular in nature, different electronics packages can be may connected to the neural interface overtime (e.g., every few days or weeks) to determine which provides the best results. In some examples, a single electronics package is used, but its settings are adjusted. In any event, while this swapping or adjusting is taking place, the implantable connector can remain outside of the skin. Once an appropriate electronics package has been identified or the proper settings have been learned, the implantable connector can be implanted under the patient's skin.

In the following, further examples are described to facilitate the understanding of the present disclosure.

Example 1

In this example, there is provided a device, including:
a first component including:
an interconnect board including a first board surface and a second board surface;
a first conductive conduit extending between a first bond pad on the first board surface and a second bond pad on the second board surface; and
an electric lead electrically connected to the first conductive conduit via the first bond pad;
a second component including:
a feedthrough substrate including a first substrate surface and a second substrate surface;
a second conductive conduit extending between a third bond pad on the first substrate surface and a fourth bond pad on the second substrate surface;
an electronic device electrically connected to the second conductive conduit via the third bond pad; and
a housing under which is disposed the electronic device and the first substrate surface;
a compressible electrical contact attached to at least one of the second bond pad or the fourth bond pad; and
a compressible gasket attached to at least one of the interconnect board or the feedthrough substrate, the compressible gasket extending about the compressible electrical contact,
wherein, when the first component and the second component are mechanically coupled, the compressible electrical contact is compressed so as to electrically connect the first conductive conduit and the second conductive conduit Example 2

In this example, there is provided a device of any of the preceding or subsequent examples, wherein, when the first component and the second component are mechanically coupled, the compressible gasket is compressed to electrically isolate the compressible electrical contact.

Example 3

In this example, there is provided a device of any of the preceding or subsequent examples, further including a mechanical coupler that mechanically couples the first component and the second component.

Example 4

In this example, there is provided a device of any of the preceding or subsequent examples, wherein the mechanical coupler includes at least one of a set of mechanical clamps, a set of screws, or a set of biased clips.

Example 5

In this example, there is provided a device of any of the preceding or subsequent examples, further including one or more alignment structures for geometrically aligning an orientation of the first component with respect to the second component.

Example 6

In this example, there is provided a device of any of the preceding or subsequent examples, wherein the interconnected board includes a lip extending around an exterior edge of the interconnected board; and engagement between the housing and the exterior edge of the interconnect board forms a mechanical coupler that mechanically couples the first component and the second component.

Example 7

In this example, there is provided a device of any of the preceding or subsequent examples, wherein:
the first conductive conduit is one of a first plurality of conductive conduits extending between first respective bond pads on the first board surface and second respective bond pads on the second board surface;
the second conductive conduit is one of a second plurality of conductive conduits extending between third respective bond pads on the first substrate surface and fourth respective bond pads on the second substrate surface;
the compressible electrical contact is one of a plurality of compressible electrical contacts; and
the compressible gasket extends around the plurality of compressible electrical contacts.

Example 8

In this example, there is provided a device of any of the preceding or subsequent examples, wherein the compressible gasket electrically isolates and physically separates the plurality of compressible electrical contacts.

Example 9

In this example, there is provided a device of any of the preceding or subsequent examples, wherein the compressible gasket includes a plurality of compressible gaskets each of which electrically isolates and physically separates a respective compressible electrical contact of the plurality of compressible electrical contact.

Example 10

In this example, there is provided a device of any of the preceding or subsequent examples, wherein:
the second respective bond pads are aligned in a first two-dimensional array; and
the fourth respective bond pads are aligned in a second two-dimensional array corresponding to the first two-dimensional array.

Example 11

In this example, there is provided a device of any of the preceding or subsequent examples, wherein individual compressible electrical contacts of the plurality of compressible electrical contacts are aligned with the first two-dimensional array and the second two-dimensional array.

Example 12

In this example, there is provided a device of any of the preceding or subsequent examples, wherein the first component further includes an epoxy insulating layer disposed on the first board surface and covering at least a portion of the electric lead.

Example 13

In this example, there is provided a device, including:
a planar board including a first set of conductive pathways extending between a first side of the planar board and a second side of the planar board;
first electrical contacts disposed on the first side of the planar board;
a first set of bond pads disposed on the second side of the planar board, the first set of bond pads electrically connected to the first electrical contacts via the first set of conductive pathways;
a planar substrate including a second set of conductive pathways extending between a first side of the planar substrate and a second side of the planar substrate;
second electrical contacts disposed on the first side of the planar substrate;
a second set of bond pads disposed on the second side of the planar substrate, the second set of bond pads electrically connected to the second electrical contacts;
a set of compressible electrical contacts extending between the first set of bond pads and the second set of bond pads; and
a mechanical coupler extending between the planar board and the planar substrate, the mechanical coupler configured to couple the planar board and the planar substrate, the set of compressible electrical contacts held in compression by the mechanical coupler so as to electrically connect the first electrical contacts and the second electrical contacts.

Example 14

In this example, there is provided a device of any of the preceding or subsequent examples, wherein the first electrical contacts form a neural interface including a plurality of electrical leads.

Example 15

In this example, there is provided a device of any of the preceding or subsequent examples, wherein the second electrical contacts comprise a set of electrical contacts electrically connected to an electronic device.

Example 16

In this example, there is provided a device of any of the preceding or subsequent examples, wherein the first electrical contacts includes a first set of electrical leads and the second electrical contacts includes a second set of electrical leads, the set of compressible electrical contacts electrically connecting individual ones of the first set of electrical leads and individual ones of the second set of electrical leads.

Example 17

In this example, there is provided a device of any of the preceding or subsequent examples, further including a compressible gasket that is held in compression by the mechanical coupler so as to electrically isolate the set of compressible electrical contacts.

Example 18

In this example, there is provided a device of any of the preceding or subsequent examples, further including a compressible gasket that is held in compression by the mechanical coupler so as to physically separate the set of compressible electrical contacts.

Example 19

In this example, there is provided a device of any of the preceding or subsequent examples, wherein each compressible electrical contact of the set of compressible electrical contacts is defined by a compression axis, each compressible electrical contact compressible in a first direction along the compression axis and extendable in a second direction along the compression axis.

Example 20

In this example, there is provided a device of any of the preceding or subsequent examples, wherein a pitch value measured between a first compressible electrical contact and a second compressible electrical contact is between 0.1 millimeters and 2 millimeters.

Example 21

In this example, there is provided a device of any of the preceding or subsequent examples, wherein the mechanical coupler includes at least one of a set of mechanical clamps, a set of screws, or a set of biased clips.

Example 22

In this example, there is provided a device of any of the preceding or subsequent examples, further including an alignment structure disposed between the planar board and the planar substrate, the alignment structure mechanically maintaining planarity between the planar board and the planar structure when the mechanical coupler couples the planar board and the planar substrate.

Example 23

In this example, there is provided a system, including:
an electronics package including:
a feedthrough substrate including a first substrate surface and a second substrate surface;
a plurality of conductive conduits extending between the first substrate surface and the second substrate surface;
a first plurality of bond pads disposed on the second substrate surface;
an electronic device electrically connected to the first plurality of bond pads via the plurality of conductive conduits; and
a housing enclosing the electronic device and the second substrate surface;
a neural interface including;
an interconnect board including a first board surface and a second board surface;
a plurality of electrical leads attached to the first board surface;
a second plurality of bond pads disposed on the second board surface, the second plurality of bond pads electrically connected to the plurality of electrical leads;
a plurality of compressible contacts attached to the second plurality of bond pads; and
a compressible gasket attached to the second board surface, the compressible contact physically separating and electrically isolated individual ones of the plurality of compressible contacts; and
a mechanical coupler configured to mechanically couple the neural interface and the electronics package so as to hold the plurality of compressible contacts in physical contact with the first plurality of bond pads.

Example 24

In this example, there is provided a system of any of the preceding or subsequent examples, wherein the second plurality of bond pads is electrically connected to the plurality of leads via a second plurality of conductive conduits formed in the interconnect board.

Example 25

In this example, there is provided a system of any of the preceding or subsequent examples, wherein the neural interface and the electronics package are adapted for subcutaneous operation.

Example 26

In this example, there is provided a method, including:
forming a set of conductive pathways in an interconnect board;
attaching a set of electrical leads to a first side of the interconnect board so as to electrically connect the set of conductive pathways and the set of electrical leads;
forming a set of bond pads on a second side of the interconnect board, the set of bond pads electrically connected to the set of conductive pathways;
attaching a set of compressible contacts to the set of bond pads; and
attaching a compressible gasket to the second side of the interconnect board, the set of compressible contacts extending through respective openings of the compressible gasket.

Example 27

In this example, there is provided a method of any of the preceding or subsequent examples, further including:
providing an electronics package that includes a set of exposed bond pads; and
coupling, via a mechanical coupler, the electronics package and the interconnect board such that the set of exposed bond pads physically contact the set of compressible contacts and the compressible gasket physically contacts the electronics package

Example 28

In this example, there is provided a method of any of the preceding or subsequent examples, wherein coupling, via the mechanical coupler, the electronics package and the interconnect board includes releasably coupling the electronics package and the interconnect board.

Example 29

In this example, there is provided a method of any of the preceding or subsequent examples, wherein:
the electronics package includes:
a feedthrough substrate including a first side and a second side;
an electronic device supported by the first side;
a housing coupled to the feedthrough substrate so as to enclose the electronic device; and
a second set of conductive conduits extending between the first side and the second side; and
the set of exposed bond pads is electrically connected to the electronic device via the second set of conductive conduits.

Example 30

In this example, there is provided a method, including:
implanting a set of electrodes of a neural interface at an incision location, the neural interface including:
a planar board including a first board side and a second board side; and
a set of conductive conduits extending through the planar board so as to electrically connect a set of compressible electrical contacts disposed on the first board side and the set of electrodes disposed on the second board side;
aligning the set of compressible electrical contacts with a corresponding set of bond pads of an electronics package; and
coupling the neural interface and the electronics package to form a coupled package.

Example 31

In this example, there is provided a method of any of the preceding or subsequent examples, further including placing the coupled package at the incision location or at a different incision location.

Example 32

In this example, there is provided a method of any of the preceding or subsequent examples, wherein:
the electronics package includes:
a planar substrate including a first planar side and a second planar side;
an electronic device supported by the first planar side;
a housing coupled to the planar substrate so as to enclose the electronic device; and
a second set of conductive conduits extending between the first planar side and the second planar side; and
the corresponding set of bond pads is electrically connected to the electronic device via the second set of conductive conduits.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

What is claimed is:

1. A device, comprising:
    a board comprising a first conductive pathway extending between a first side of the board and a second side of the board;
    a first electrical contact disposed on the first side of the board;
    a first bond pad disposed on the second side of the board, the first bond pad electrically connected to the first electrical contact via the first conductive pathway;
    a substrate comprising a second conductive pathway extending between a first side of the substrate and a second side of the substrate;
    a second electrical contact disposed on the first side of the substrate;
    a second bond pad disposed on the second side of the substrate, the second bond pad electrically connected to the second electrical contact;
    a compressible electrical contact extending between the first bond pad and the second bond pad; and
    a compressible gasket disposed between the board and the substrate, wherein the compressible gasket is configured to electrically isolate and hermetically isolate the compressible electrical contact when the compressible electrical contact is held in compression between the first bond pad and the second bond pad.

2. The device of claim 1, further comprising a mechanical coupler extending between the board and the substrate, the mechanical coupler configured to couple the board and the substrate.

3. The device of claim 2, wherein the compressible electrical contact is held in compression between the first bond pad and the second bond pad by the mechanical coupler so as to electrically connect the first electrical contact and the second electrical contact.

4. The device of claim 2, wherein the compressible gasket is configured to electrically isolate the compressible electrical contact from other compressible electrical contacts.

5. The device of claim 2, wherein the compressible gasket physically separates the first electrical contact from other electrical contacts.

6. The device of claim 2, wherein the mechanical coupler comprises at least one of a set of mechanical clamps, a set of screws, or a set of biased clips.

7. The device of claim 2, further comprising an alignment structure disposed between the board and the substrate.

8. The device of claim 7, wherein the alignment structure comprises a plurality of elements having a uniform height and configured to maintain planarity between the board and the substrate when the mechanical coupler couples the board and the substrate.

9. The device of claim 1, wherein at least one of the first side of the substrate or the second side of the substrate is planar.

10. The device of claim 1, wherein at least one of the first side of the board or the second side of the board is planar.

11. The device of claim 1, wherein the first electrical contact forms a neural interface comprising a plurality of electrical leads.

12. The device of claim 1, wherein the second electrical contact comprises a set of electrical contacts electrically connected to an electronic device.

13. The device of claim 1, wherein the first electrical contact comprises a first electrical lead and the second electrical contact comprises a second electrical lead, the compressible electrical contact electrically connecting the first electrical lead and the second electrical lead.

14. The device of claim 1, wherein the compressible electrical contact is aligned along a compression axis and is compressible in a first direction along the compression axis and extendable in a second direction along the compression axis.

15. A system, comprising:
an electronics package comprising:
  a feedthrough substrate comprising a first substrate surface and a second substrate surface;
  a conductive conduit extending between the first substrate surface and the second substrate surface;
  a first bond pad disposed on the second substrate surface;
  an electronic device electrically connected to the first bond pad via the conductive conduit;
a neural interface comprising;
  an interconnect board comprising a first board surface and a second board surface;
  an electrical lead attached to the first board surface;
  a second bond pad disposed on the second board surface, the second bond pad electrically connected to the electrical lead;
  a compressible contact attached to the second bond pad; and
  a compressible gasket attached to the second board surface, wherein the compressible gasket is configured to physically separate, hermetically isolate, and electrically isolate the compressible contact when the compressible contact is held in compression between the first bond pad and the second bond pad.

16. A method, comprising:
forming a conductive pathway in an interconnect board;
attaching an electrical lead to a first side of the interconnect board to electrically connect the conductive pathway and the electrical lead;
forming a bond pad on a second side of the interconnect board, the bond pad electrically connected to the conductive pathway;
attaching a compressible contact to the bond pad; and
attaching a compressible gasket to the second side of the interconnect board, the compressible contact extending through an opening of the compressible gasket, wherein the compressible gasket is configured to electrically isolate and hermetically isolate the compressible contact when the compressible contact is held in compression between the bond pad and a different bond pad.

17. The method of claim 16, further comprising:
providing an electronics package that comprises the different bond pad; and
aligning the different bond pad and the compressible contact;
aligning the compressible gasket and the electronics package; and
coupling, via a mechanical coupler, the electronics package and the interconnect board, with the different bond pad physically contacting the compressible contact and the compressible gasket physically contacting the electronics package.

18. The method of claim 17, wherein coupling, via the mechanical coupler, the electronics package and the interconnect board comprises releasably coupling the electronics package and the interconnect board.

19. The device of claim 1, wherein the compressible gasket is formed from a biocompatible silicone.

20. The device of claim 1, further comprising an insulating material disposed on the second bond pad and the compressible electrical contact, the insulating material configured to further electrically isolate the compressible electrical contact.

* * * * *